US008128564B2

United States Patent
Kwon et al.

(10) Patent No.: US 8,128,564 B2
(45) Date of Patent: Mar. 6, 2012

(54) APPARATUS AND METHOD FOR IMAGING SHEAR MODULUS WITHIN A BODY

(75) Inventors: Oh In Kwon, Seoul (KR); Eung Je Woo, Seongnam-si (KR); Chun Jae Park, Seoul (KR); Hyun Soo Nam, Seoul (KR)

(73) Assignee: University-Industry Cooperation Group of Kyunghee University, Yongin (KR)

( * ) Notice: Subject to any disclaimer, the term of this patent is extended or adjusted under 35 U.S.C. 154(b) by 1000 days.

(21) Appl. No.: 12/098,299

(22) Filed: Apr. 4, 2008

(65) Prior Publication Data

US 2009/0007674 A1 Jan. 8, 2009

(30) Foreign Application Priority Data

Apr. 4, 2007 (KR) .................. 10-2007-0033234

(51) Int. Cl.
*A61B 8/00* (2006.01)
(52) U.S. Cl. ......... 600/438; 600/407; 600/410; 600/437
(58) Field of Classification Search .................. 600/407, 600/437, 438, 410
See application file for complete search history.

(56) References Cited

U.S. PATENT DOCUMENTS

| 5,474,070 A | 12/1995 | Ophir et al. | |
| 7,775,980 B2 * | 8/2010 | Sumi | 600/442 |
| 2004/0034304 A1 * | 2/2004 | Sumi | 600/439 |
| 2006/0264736 A1 | 11/2006 | Ehman | |

FOREIGN PATENT DOCUMENTS

JP 2003-210460 A 7/2003

OTHER PUBLICATIONS

International Search Report and written opinion dated Jul. 28, 2008 as received in application No. PCT/KR2008/001921.
Korean Office Action dated Mar. 18, 2008 as received in application No. 9-5-2008-014964367.
Korean Notice of Allowance dated Sep. 29, 2008 as received in application No. 9-5-2008-05013266.
Venkatest et al., MR Elastography of Liver Tumors: Preliminary Results, Hepatobiliary Imaging, Original Research, Jun. 2008, pp. 1534-1540.
Sandrin et al., Shear Modulus Imaging with 2-D Transient Elastography, IEEE Transactions on Ultrasonics, Ferroelectrics, and Frequency Control, Apr. 2002, pp. 426-436, vol. 49, No. 4.

* cited by examiner

*Primary Examiner* — Brian Casler
*Assistant Examiner* — Amanda Lauritzen
(74) *Attorney, Agent, or Firm* — Maschoff Gilmore & Israelsen

(57) ABSTRACT

An apparatus and method for imaging a shear modulus within a body is disclosed. A method for imaging a shear modulus in accordance with the present invention includes generating an elastic wave inside an object to be measured; detecting the elastic wave ongoing inside the object to be measured; calculating a shear modulus of the inside of the object to be measured, based on a value obtained by differentiating the detected elastic wave one time; and imaging the inside of the object to be measured, based on the calculated shear modulus.

10 Claims, 2 Drawing Sheets

APPARATUS AND METHOD FOR IMAGING SHEAR MODULUS WITHIN A BODY

This application claims the benefit of the Korean Patent Application No. 10-2007-0033234, filed on Apr. 4, 2007, which is hereby incorporated by reference as if fully set forth herein.

BACKGROUND OF THE INVENTION

1. Field of the Invention

The present invention relates to an apparatus and method for imaging the inside of an object to be measured, by using an elastic wave.

2. Discussion of the Related Art

Generally, X-rays, magnetic resonance imaging (MRI) and supersonic waves have been used to image an inner structure of a body or an object. New medical imaging methods have been developed to overcome limitation of the existing medial imaging field.

For example, a method for imaging a shear modulus within a body has been developed. According to this method, a wave generator, which generates a shear wave, is attached to a surface of a body, and the shear wave generated within the body through the wave generator is measured using MRI. Afterwards, the shear modulus within the body is imaged using displacement of the measured shear wave.

It is known that a cancer tissue within the body has a shear modulus different from a normal tissue due to its variable physical properties. Such a variation of physical properties is imaged using displacement of the shear wave that can be measured using MRI equipment, whereby many studies for new medical imaging are being made actively.

However, considering that the measured shear wave displacement data include noise, various shear modulus imaging methods, which have been conventionally developed, have a drawback in that it is difficult to image a real wrong tissue due to amplified noise.

SUMMARY OF THE INVENTION

Accordingly, the present invention is directed to an apparatus and method for imaging a shear modulus within a body, which substantially obviates one or more problems due to limitations and disadvantages of the related art.

An object of the present invention is to provide an apparatus and method for imaging a shear modulus within a body, in which the inside of an object to be measured can exactly be imaged using an elastic wave.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a method for imaging a shear modulus in accordance with the present invention includes generating an elastic wave inside an object to be measured; detecting the elastic wave ongoing inside the object to be measured; calculating a shear modulus of the inside of the object to be measured, based on a value obtained by differentiating the detected elastic wave one time; and imaging the inside of the object to be measured, based on the calculated shear modulus.

The step of calculating a shear modulus of the inside of the object to be measured, based on a value obtained by differentiating the detected elastic wave one time includes calculating an irrotational component and a solenoidal component of a stress vector from the detected elastic wave; and calculating the shear modulus of the inside of the object to be measured, using the calculated irrotational component, the calculated solenoidal component, and the value obtained by differentiating the detected elastic wave one time.

The step of calculating an irrotational component and a solenoidal component from the detected elastic wave includes calculating the irrotational component using one directional component value of the detected elastic wave and a frequency of the elastic wave; and calculating the solenoidal component based on the calculated irrotational component and the value obtained by differentiating the detected elastic wave one time.

In the step of calculating the shear modulus of the inside of the object to be measured, using the calculated irrotational component, the calculated solenoidal component, and the value obtained by differentiating the detected elastic wave one time, the solenoidal component approximate to an actual value is calculated by applying the calculated irrotational component and the value obtained by differentiating the detected elastic wave one time to an iteration algorithm.

In another aspect of the present invention, an apparatus for imaging a shear modulus includes an elastic wave generator generating an elastic wave inside an object to be measured; a signal detector detecting the elastic wave ongoing inside the object to be measured; and a controller calculating a shear modulus of the inside of the object to be measured, based on a value obtained by differentiating the detected elastic wave one time, and imaging the inside of the object to be measured, based on the calculated shear modulus.

The signal detector is MRI equipment or a supersonic measurement device.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Hereinafter, the preferred embodiments of the present invention will be described with reference to the accompanying drawings.

Figure 1:
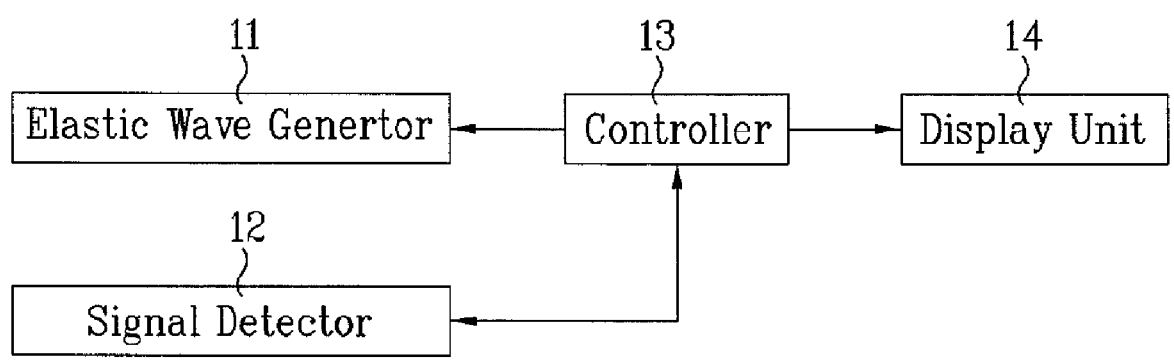
FIG. 1 illustrates an apparatus for imaging a shear modulus in accordance with the present invention.

FIG. 1 illustrates an apparatus for imaging a shear modulus in accordance with the present invention. FIG. 1 illustrates only elements required to describe the subject matter of the present invention. As shown in FIG. 1, the apparatus for imaging a shear modulus in accordance with the present invention includes an elastic wave generator 11 providing an elastic wave into an object to be measured, a signal detector 12 detecting the elastic wave ongoing inside the object, a controller 13 outputting image data based on the signal detected from the signal detector 12, and a display unit 14 displaying the image data output from the controller 13.

The elastic wave includes a longitudinal wave and a transverse wave. The longitudinal wave (compressed wave) is generated due to bulk modulus accompanied with bulk change caused by oscillation displacement of an elastic medium in parallel with an ongoing direction of the wave. The transverse wave (shear wave) is generated due to form change caused by oscillation displacement of an elastic medium vertically with an ongoing direction of the wave. In this case, the elastic wave provided into the object to be measured by the elastic wave generator 11 is a shear wave. A shear wave generator or a supersonic generator is used as the elastic wave generator 11.

A method for imaging the inside of the object to be measured using the aforementioned imaging apparatus will be described below.

First of all, the elastic wave generator 11 generates an elastic wave of a frequency ($\omega$) set under the control of the controller 13, and provides the generated elastic wave to a surface of the object to be measured. The elastic wave provided into the object to be measured and ongoing therein is detected by the signal detector 12.

Figure 2:
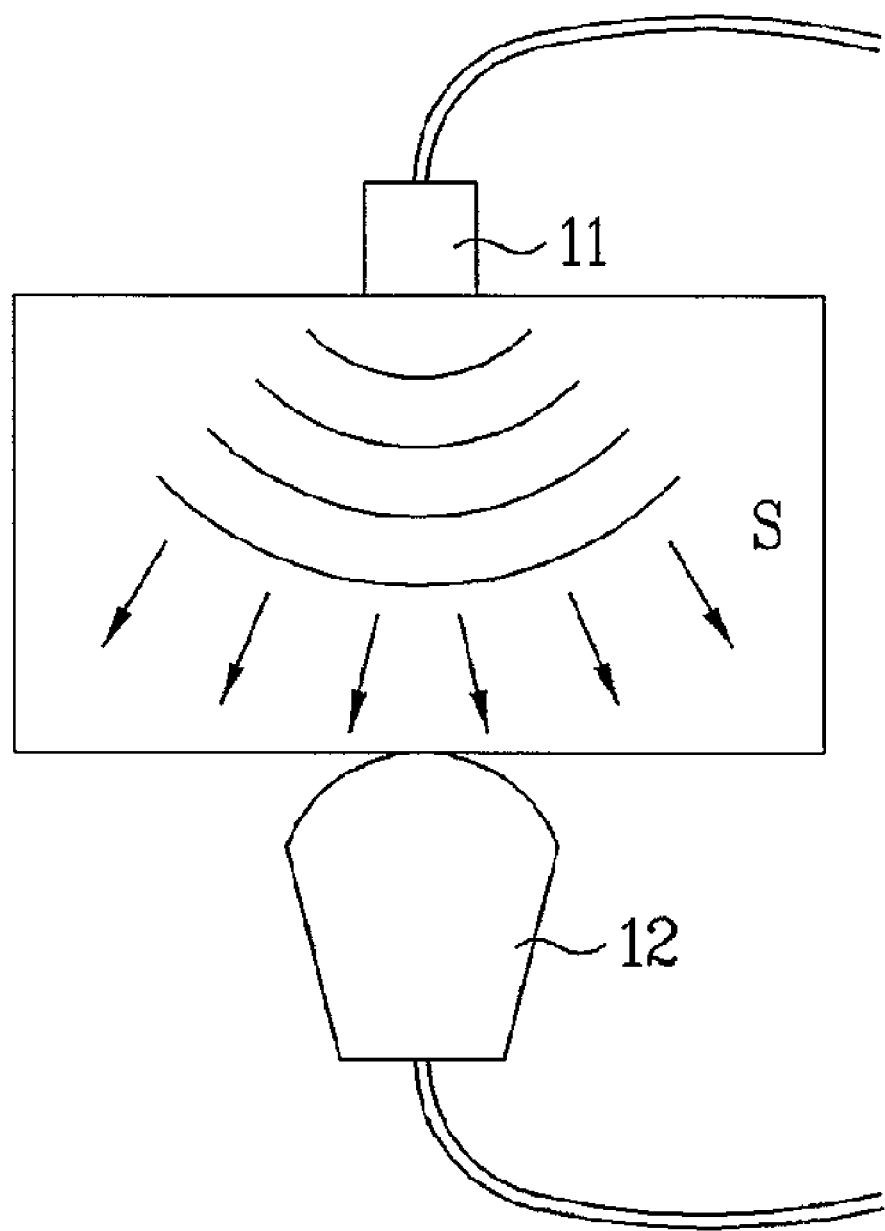
FIG. 2 illustrates a part of an apparatus for imaging a shear modulus in accordance with the present invention.

An MRI scanner or a supersonic measurement device can be used as the signal detector 12. For example, if the MRI scanner is used as the signal detector 12, the object to be measured can be scanned by a large-scaled MRI scanner in a non-contact state to measure the elastic wave ongoing inside the object to be measured. If a small-scaled supersonic measurement device is used as the signal detector 12, it is preferable that a part of the object S to be measured is located on a virtual straight line which connects the elastic wave generator 11 with the supersonic measurement device 12 as shown in FIG. 2, and is in contact with the supersonic measurement device 12.

The signal detected by the signal detector 12 is transmitted to the controller 13, and the controller 13 outputs image data that can image the inside of the object S to be measured, based on the detected signal.

A method for generating image data based on the detected signal is as follows. The present invention suggests two methods for generating image data based on the detected elastic wave signal.

First Method

An elastic wave signal (elastic displacement) U=(Ux, Uy, Uz) detected by the signal detector 12 is expressed in a frequency domain under the assumption of isotropy and linearity of a medium in the form of a partial differential equation such as the following equation 1.

$$\nabla \cdot (\mu \nabla u) + \nabla ((\lambda = \mu) \nabla \cdot u) + \rho \omega^2 u = 0 \quad \text{[Equation 1]}$$

In the equation 1, $\lambda$ represents a longitudinal modulus or a bulk modulus of an object to be measured, and $\mu$ represents a transverse modulus or a shear modulus of an object to be measured. Also, $\omega$ represents a frequency of the elastic wave.

In order to apply the Equation 1 to an algorithm of the present invention, supposing incompressibility having no bulk change of the object to be measured, due to a given force, the equation 1 satisfies the following equation 2.

$$\nabla \cdot \mu \nabla U + \omega^2 U = 0 \quad \text{[Equation 2]}$$

To image the inside of the object to be measured, it is necessarily required to recover the shear modulus $\mu$ from the measured elastic wave signal U=(Ux, Uy, Uz). To induce an equation for obtaining the shear modulus $\mu$, it is supposed that the shear modulus $\mu$ is a constant. Under such assumption, the equation 2 can be expressed in a simpler form such as the following equation 3.

$$\mu \nabla^2 U + \omega^2 U = 0 \quad \text{[Equation 3]}$$

The shear modulus $\mu$ of Uz, which is one of components of the measured elastic wave signal, is expressed by the following equation 4 using the equation 3.

$$\mu = -\frac{\omega^2 U_z}{\nabla^2 U_z} \quad \text{[Equation 4]}$$

As expressed by the equation 4, the shear modulus p according to the first method has a great negative value if the frequency $\omega$ of the elastic wave becomes great but has a small negative value if the elastic wave signal Uz differentiated twice becomes great.

The controller 13 calculates the shear modulus p from the measured elastic wave signal U=(Ux, Uy, Uz) by using the equation 4, generates image data based on the measured elastic wave signal U=(Ux, Uy, Uz) and the calculated shear modulus p, and outputs the generated image data to the display unit 14. It will be apparent that generating image data based on the measured elastic wave signal U=(Ux, Uy, Uz) and the calculated shear modulus $\mu$ can be carried out by various methods. In this case, the calculated shear modulus $\mu$ represents a modulus of body tissues inside the object to be measured. Since the respective tissues have different moduli, the image data generated based on the shear modulus $\mu$ can image the inside of the object to be measured.

Second Method

Since the first method differentiates the measured elastic wave signal Uz twice, a value of noise included in the elastic wave signal may also be differentiated twice. In other words, if noise is included in the elastic wave signal, the value of noise can be amplified as much as differentiation of twice. The second method is to minimize such amplification of noise.

When the Equation 2 is expressed by an equation of a z-directional component Uz of the measure elastic wave signal, the following equation 5 can be obtained.

$$\nabla \cdot \mu \nabla U_z + \omega^2 U_z = 0 \quad \text{[Equation 5]}$$

In the equation 5, the stress part $\mu \nabla U_z$ in the simplified equation including an unfixed parameter $\mu$ can be expressed by the following equation 6 in accordance with Helmholtz decomposition.

$$\mu \nabla U_z = \nabla f + \nabla \times W \quad \text{[Equation 6]}$$

In other words, the vector field $\mu \nabla U_1$ is divided into an irrotational component and a solenoidal component in accordance with Helmholtz decomposition. In this case, the irrotational component represents a gradient value of scalar potential f, and the solenoidal component represents a curl value of vector potential W.

Also, the equation 6 can be substituted for the equation 5 to obtain the following equation 7.

$$\nabla \cdot (\nabla f + \nabla \times W) + \omega^2 U_z = 0 \quad \text{[Equation 7]}$$

The equation 7 can be expressed as follows to obtain the scalar potential f.

$$\nabla^2 f = -\omega^2 U_z \quad \text{[Equation 8]}$$

In the equation 8, since a value of a right side represents a set frequency and the measured elastic wave signal, a function value of the scalar potential f can be obtained using the equation 8. A gradient component of a stress vector can be obtained using the obtained potential f, and if the curl value of the vector potential W of the solenoidal component is disregarded, an equation that can obtain the shear modulus μ can be induced using the equation 6. For example, if the vector product of ∇Uz is taken at both sides of the equation 6, the following equation 9 can be obtained.

$$\mu \nabla U_z \cdot \nabla U_z = \nabla f \cdot \nabla U_z + \nabla \times W \cdot \nabla U_z \quad \text{[Equation 9]}$$

If the equation 9 is arranged to recover the curl component repeatedly, the following equation 10 for obtaining the shear modulus μ can be induced.

$$\mu^{n+1} = \frac{\nabla f \cdot \nabla U_z + \nabla \times W^n \cdot \nabla U_z}{\nabla U_z \cdot \nabla U_z} \quad \text{[Equation 10]}$$

$$n = 0, 1, 2, 3 \ldots$$

The equation 10 is for an iteration algorithm which obtains the most approximate value in a repeated manner. Since the function value of f is calculated through the equation 8 and Uz is the measured value, a value of the shear modulus μ can be obtained if ∇×W$^n$ is obtained.

After elastic displacement $U_z^n$ corresponding to a shear modulus $\mu^n$ which is improved repeatedly is calculated, a divergence-free part of $\mu^n U_z^n$ can be obtained by calculation.

$$\mu^n \nabla U_z^n = \nabla f^n - \Delta \times W^n \quad \text{[Equation 11]}$$

$$\nabla \cdot (\mu^n \nabla U_z^n) + \omega^2 U_z^n = C \quad \text{[Equation 12]}$$

For example, after $U_z^n$ is calculated using the equation 12, a value of ∇×W$^n$ for the shear modulus $\mu^n$ is calculated using the equation 11. Subsequently, if the calculated value of ∇×W$^n$ is substituted for the equation 10, a shear modulus $\mu^{n+1}$ can be obtained.

The shear modulus $\mu^{n+1}$ is substituted for the equation 11 to calculate ∇×W$^{n+1}$, and the calculated value of ∇×W$^{n+1}$ is substituted for the equation 10 to calculate a shear modulus $\mu^{n+2}$. In this case, the shear modulus becomes more approximate to the actual shear modulus if the value of n increases.

In case of an anisotropic modulus, if μ is expressed by 3×3 matrix, for example, after the elastic displacements Ux, Uy, Uz in three directions are measured, fx, fy, fz with respect to the respective directions are respectively obtained using the equation 8. If W is equal to 0, the following equation 13 can be obtained using the equation 6.

$$\mu[\nabla U_x, \nabla U_y, \nabla U_z] = [\nabla f_x, \nabla f_y, \nabla f_z] \quad \text{[Equation 13]}$$

An anisotropic modulus matrix μ can be obtained using the following equation 14.

$$\mu = [\nabla U_x, \nabla U_y, \nabla U_z^{-1}][\nabla f_x, \nabla f_y, \nabla f_z] \quad \text{[Equation 14]}$$

The controller 13 calculates the shear modulus in accordance with the aforementioned method, and generates and outputs image data based on measured elastic wave signal U=(Ux, Uy, Uz) and the calculated shear modulus μ.

According to the second method, since the shear modulus is calculated using a value $\nabla U_z$ of the elastic wave signal differentiated one time, an amplification level of noise is lowered. Accordingly, it is possible to obtain modulus image robust to noise. Also, since a modulus approximate to an actual value is calculated using the iteration algorithm, it is possible to obtain exact modulus image.

The modulus image can be used to detect a focus by imaging the inside of a body or animal. Also, the modulus image can be applied to all the fields for imaging the elastic wave.

As described above, the apparatus and method for imaging a shear modulus within a body in accordance with the present invention has the following advantages.

Since the shear modulus which minimizes noise is provided, it is possible to reproduce image of high picture quality, which cannot be obtained from the existing MRI equipment or supersonic measurement device.

In addition, the modulus image of the present invention can be applied to the existing medical equipment. Accordingly, functional imaging can be provided to internal organs having different shear moduli, whereby a new medical checkup technique can be achieved.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A method for imaging a shear modulus, the method comprising:
    generating an elastic wave inside an object to be measured,
        wherein the elastic wave being a shear wave and wherein the elastic wave is generated by a shear wave generator or a supersonic generator;
    measuring the elastic wave ongoing inside the object to be measured,
        wherein the elastic wave is measured by MRI equipment or a supersonic measurement device;
    calculating a shear modulus of the inside of the object to be measured, based on a value obtained by differentiating the measured elastic wave one time,
        wherein the shear modulus is calculated by a controller using the measured elastic wave, and
        wherein the calculating of the shear modulus includes:
            calculating an irrotational component and a solenoidal component of a stress vector from the measured elastic wave; and
            calculating the shear modulus of the inside of the object to be measured, by using the calculated irrotational component, the calculated solenoidal component, and the value obtained by differentiating the measured elastic wave one time; and
    imaging the calculated shear modulus in the inside of the object, wherein the inside of the object is displayed by a display unit.

2. The method as claimed in claim 1, wherein the step of calculating the irrotational component and the solenoidal component from the measured elastic wave includes:
    calculating the irrotational component by using one directional component value of the measured elastic wave and a frequency of the elastic wave; and
    calculating the solenoidal component based on the calculated irrotational component and the value obtained by differentiating the measured elastic wave one time.

3. The method as claimed in claim 1, wherein in the step of calculating the shear modulus of the inside of the object to be measured, using the calculated irrotational component, the calculated solenoidal component, and the value obtained by differentiating the measured elastic wave one time, the solenoidal
component approximate to an actual value is calculated by applying the calculated irrotational component and the value obtained by differentiating the measured elastic wave one time to an iteration algorithm.

4. The method as claimed in claim 1, wherein the step of calculating the shear modulus of the inside of the object to be measured, based on a value obtained by differentiating the measured elastic wave one time includes:
calculating a three-directional irrotational component and a three-directional solenoidal component of a stress vector from the measured elastic wave; and
calculating an anisotropic shear modulus of the inside of the object to be measured, by using the calculated irrotational component, the calculated solenoidal component, and the value obtained by differentiating the measured elastic wave one time.

5. The method as claimed in claim 4, wherein the step of calculating the three-directional irrotational component and the three-directional solenoidal component from the measured elastic wave includes:
calculating the three-directional irrotational component by using a three-directional component value of the detected measured elastic wave and a frequency of the elastic wave; and
calculating the three-directional solenoidal component based on the calculated three-directional irrotational component and the value obtained by differentiating the measured elastic wave one time.

6. An apparatus for imaging a shear modulus, the apparatus comprising:
an elastic wave generator configured to generate an elastic wave inside an object to be measured, wherein the elastic wave generator is a shear wave generator or a supersonic generator;
a signal detector configured to measure the elastic wave ongoing inside the object to be measured, wherein the signal detector is MRI equipment or a supersonic measurement device; and
a controller configured to calculate a shear modulus of the inside of the object to be measured, based on a value obtained by differentiating the measured elastic wave one time, and imaging the calculated shear modulus in the inside of the object, wherein the controller calculates an irrotational component and a solenoidal component of a stress vector from the measured elastic wave, and calculates the shear modulus of the inside of the object to be measured, by using the calculated irrotational component, the calculated solenoidal component, and the value obtained by differentiating the measured elastic wave one time.

7. The apparatus as claimed in claim 6, wherein the controller calculates the irrotational component by using one directional component value of the measured elastic wave and a frequency of the elastic wave, and calculates the solenoidal component based on the calculated irrotational component and the value obtained by differentiating the measured elastic wave one time.

8. The apparatus as claimed in claim 6, wherein the controller calculates the solenoidal component approximate to an actual value by applying the calculated irrotational component and the value obtained by differentiating the measured elastic wave one time to an iteration algorithm.

9. The apparatus as claimed in claim 6, wherein the controller calculates a three-directional irrotational component and a three-directional solenoidal component of a stress vector from the measured elastic wave, and calculates an anisotropic shear modulus of the inside of the object to be measured, by using the calculated irrotational component, the calculated solenoidal component, and the value obtained by differentiating the measured elastic wave one time.

10. The apparatus as claimed in claim 9, wherein the controller calculates the three-directional irrotational component by using a three-directional component value of the measured elastic wave and a frequency of the elastic wave, and calculates the three-directional solenoidal component based on the calculated three-directional irrotational component and the value obtained by differentiating the measured elastic wave one time.

* * * * *